United States Patent [19]

Evard et al.

[11] Patent Number: 4,981,478

[45] Date of Patent: Jan. 1, 1991

[54] COMPOSITE VASCULAR CATHETER

[75] Inventors: Philip C. Evard, Palo Alto; Timothy R. Machold, Moss Beach; Bojana Spahic, Temecula, all of Calif.

[73] Assignee: Advanced Cardiovascular Systems, Santa Clara, Calif.

[21] Appl. No.: 241,047

[22] Filed: Sep. 6, 1988

[51] Int. Cl.$^5$ ............................................. A61M 25/00
[52] U.S. Cl. .................................. 604/282; 128/772; 606/194
[58] Field of Search ............... 128/343, 344, 348.1, 128/772; 604/282

[56] References Cited

U.S. PATENT DOCUMENTS

| | | | |
|---|---|---|---|
| 2,472,485 | 6/1949 | Krippendorf | 604/282 X |
| 3,416,531 | 12/1968 | Edwards | 128/658 |
| 3,485,234 | 12/1969 | Stevens | 128/658 |
| 3,498,286 | 3/1970 | Polanyi et al. | 128/658 |
| 3,598,126 | 8/1971 | Hoeltzenbein | 604/282 |
| 3,773,034 | 11/1973 | Burns et al. | 604/95 |
| 3,924,632 | 12/1975 | Cook | 604/282 |
| 4,425,919 | 1/1984 | Alston, Jr. et al. | 128/658 |
| 4,448,195 | 5/1984 | LeVeen et al. | 128/344 |
| 4,572,186 | 2/1986 | Gould et al. | 128/341 |
| 4,577,543 | 3/1986 | Wilson | 87/11 |
| 4,637,396 | 1/1987 | Cook | 604/282 |
| 4,702,252 | 10/1987 | Brooks et al. | 128/344 |
| 4,706,670 | 11/1987 | Anderson et al. | 128/344 |
| 4,817,613 | 4/1989 | Jaraczewski et al. | 604/282 X |
| 4,838,268 | 6/1989 | Keith et al. | 128/344 |

Primary Examiner—C. Fred Rosenbaum
Assistant Examiner—Corrine Maglione
Attorney, Agent, or Firm—Fulwider, Patton, Lee & Utecht

[57] ABSTRACT

An improved vascular catheter having a tubular member of composite structure with a tubular substrate and a resin-impregnated fibrous covering extending over a substantial part of the length thereof. The tubular substrate which is longitudinally flexible but relatively inextendible, is preferably polyimide tubing with a lubricious coating on the inner surface thereof defining an inner lumen. The fibrous covering is preferably epoxy-impregnated aramid or polyester (Dacron) multi-filament fibers. The strands are is snugly wrapped about the tubular substrate and then impregnated with a suitable resin. One or more of the strands in the distal portion are at an angle with respect to the longitudinal axis of the tubular substrate between about 20° and about 45° greater than the angle of one or more strands in the proximal portion. Individual strand wraps in the distal portion are at an angle of about 60° to about 85° and strand wraps in such as the proximal portion are at an angle of about 30° to about 60°. The composite tubular member is preferably utilized in balloon dilatation catheters used in angioplasty procedures.

24 Claims, 2 Drawing Sheets

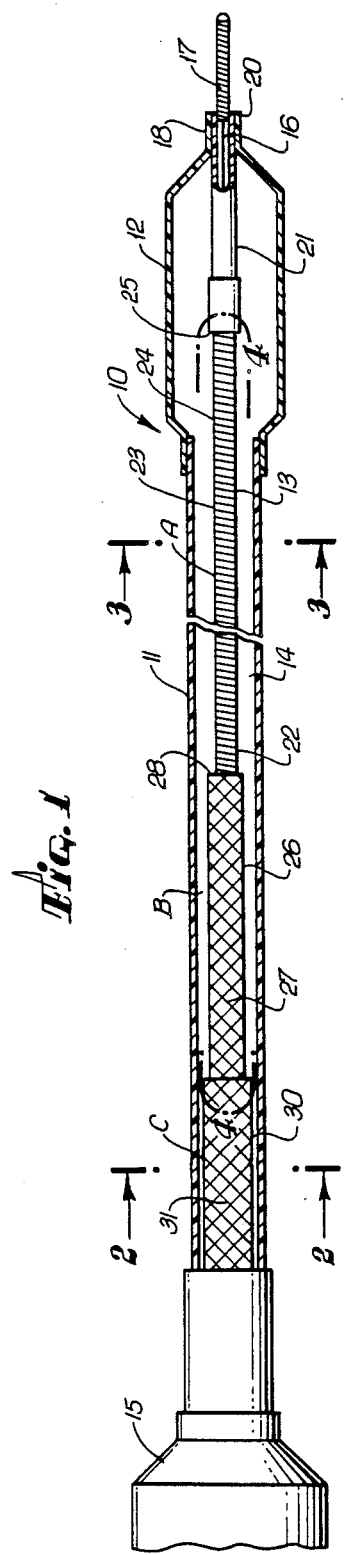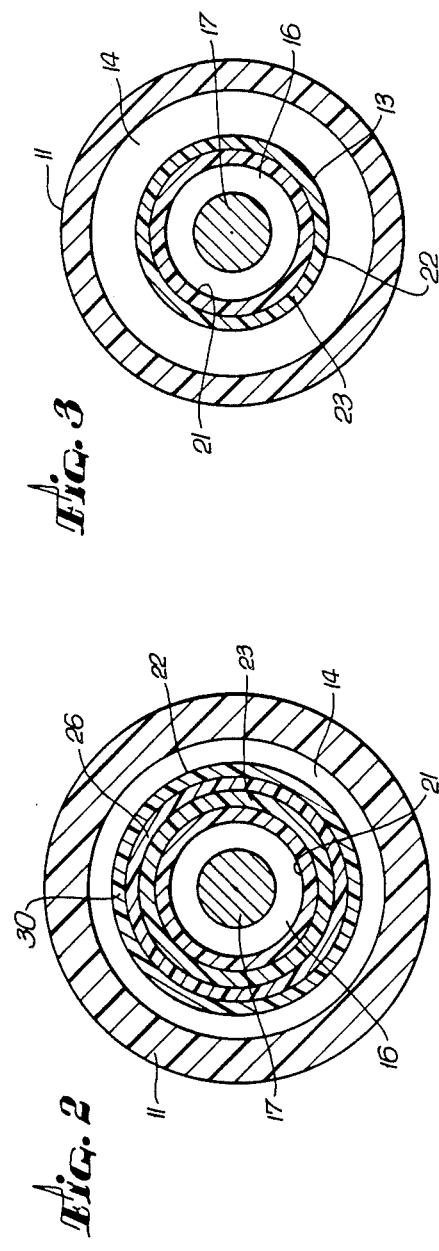

COMPOSITE VASCULAR CATHETER

BACKGROUND OF THE INVENTION

This invention generally relates to vascular catheters and particularly to catheters for vascular procedures such as percutaneous transluminal coronary angioplasty (PTCA).

In typical PTCA procedures, a guiding catheter having a performed distal tip is percutaneously introduced into the cardiovascular system of a patient and advanced therein until the distal tip of the guiding catheter is in the ostium of the desired coronary artery. A guidewire and a balloon dilatation catheter are introduced into the patient's vascular system through the previously introduced guiding catheter. The guidewire is first advanced out of the distal tip of the guiding catheter into the patient's coronary vasculature until the distal end of the guidewire crosses the lesion to be dilated. The dilatation catheter, having an inflatable balloon on the distal portion thereof, is advanced over the previously positioned guidewire, with the guidewire slidably disposed within an inner lumen of the dilatation catheter, until the dilatation balloon is properly positioned across the lesion. Once in position across the lesion, the flexible, relatively inelastic balloon is inflated to a predetermined size with radiopaque liquid at relatively high pressures (e.g., at least 100 psi) to radially compress the atherosclerotic plaque of the lesion against the inside of the artery wall. The balloon is then deflated so that the blood flow can resume through the dilated artery and the catheter can be removed.

Further details of angioplasty procedures and the devices used in such procedures, can be found in U.S. Pat. No. 4,332,254 (Lundquist); U.S. Pat. No. 4,323,071 (Simpson-Robert); U.S. Pat. No. 4,468,224 (Enzmann et al.) U.S. Pat. No. 4,516,972 (Samson); U.S. Pat. No. 4,528,622 (Samson et al.(; and U.S. Pat. No. 4,616,652 (Simpson) which are hereby incorporated herein in their entirety.

It is generally desirable to make the deflated profile of a dilatation catheter as small as possible because a smaller profile allows the catheter to pass through tighter lesions and to be advanced much further into the patient's coronary anatomy. However, if the diameter of the guidewire is reduced in order to reduce the profile of the catheter, the ability of the guidewire to transmit torsional and axial forces is likewise reduced. Heretofore, movable guidewires utilized in coronary angioplasty typically have been on the order of 0.012–00.018 inch (0.305–0.457 mm) in diameter. Attempts have been made to use smaller diameter movable guidewires in angioplasty procedures, but such smaller diameter guidewires could not always effectively transmit torque for steering the guidewire from the proximal to the distal ends, particularly when the guidewire was disposed in the patient's tortuous coronary vasculature. Moreover, small diameter movable guidewires did not always have the pushability to be readily advanced through the tortuous coronary vasculature without buckling.

Reducing the wall thickness of the tubular members which make up the catheters, can also reduce the profile, but as with reducing the diameter of the guidewire, there is a limit on how much the wall thickness of the tubular members can be reduced without detrimentally affecting the performance of the catheter. For example, if the wall thickness is reduced to such an extent that the circularity of the inner member of a dilatation catheter cannot be maintained during the placement of the catheter within the patient's vasculature, i.e., the tubular member kinks. Any guidewire disposed within the tubular member in such a case would become bound within the inner lumen thereof and could not be further advanced. This factor is particularly important with dilatation catheters in which there are very small differences in size between the outer diameter of the guidewire and the inner diameter of the lumen in the inner tubular member, such as those described in co-pending application Ser. No. 220,563, filed July 18, 1988, entitled Vascular Catheters.

What has been needed and heretofore unavailable is a dilatation catheter assembly which has a substantially reduced profile with essentially no loss in performance characteristics. The present invention satisfies that need.

SUMMARY OF THE INVENTION

This invention is directed to a flexible, dilatation catheter having excellent pushability and having sufficient diametrical rigidity to maintain the circularity of the transverse cross sections of the tubular members even when bent through arcs having relatively small radii of curvature.

The dilation catheter in accordance with the present invention in the most general sense includes a tubular member which provides longitudinal flexiblity with diametrical rigidity and which comprises a thin-walled tubular substrate formed from material such as polyimide which is coated with resin-impregnated fiber or strands such as aramid, nylon, or polyester fiber which have been wound or braided onto the tubular substrate. In dilatation catheters of concentric tubular construction having an outer tubular member with a flexible, relatively inelastic inflatable balloon member on the distal portion thereof and an inner tubular member disposed within the outer tubular member.

The resin-impregnated, fibrous coating is applied onto the tubular substrate to provide a decrease in stiffness and a corresponding increase in flexibility from the proximal to the distal portions of the tubular member. The angle of inclination of the strands is varied as it is applied to the tubular substrate as well as the thickness of the coating to control the stiffness and flexibility of the tubular member.

Strands in the distal portions are wrapped about the tubular substrate at an angle with respect to the longitudinal axis thereof from 20° to about 45° greater than the orientation of one or more strands in the proximal portion. The strands are generally wrapped around the inner tubular support member in the distal portion at an angle of inclination with respect to the axis of the tubular support member (i.e. wrap angle) of about 65° to about 85° where flexibility is desired. However, in proximal portions where some degree of stiffness is desired, the wrap angle is about 30° to about 60°. As a result of the variation in the wrap angle, the spacing between the individual wraps also vary. For example, in the proximal portion where the wrap angle is relatively small, e.g., 45°, the strand spacing may range from about 2 to 6 times the width of the individual wrapped strand, whereas in the distal portion where the wrap angle is relatively large, e.g., 80°, the fibers may be immediately adjacent to one another. The strands are preferably multi-filament fibers and there is a tendency for these fibers to spread when snugly wrapped about the tubular substrate member. The first layer of wrapped resin-impregnated fiber generally extends distally along the tubular support member the greatest distance from the proximal end thereof. The subsequent layer or group of layers, will extend distally a lesser distance than the preceding layer, thus providing increased thickness and as a result, increased stiffness in the proximal end.

Generally, each fibrous layer is wrapped from the proximal end of the tubular support member to the desired distal terminal point at a desired angle or angles. The direction of wrapping is reversed at the distal terminal point, with the inclination angle remaining the same but in a direction 90° from the first direction and the wrapping is continued to the proximal end of the tubular support member. Usually, the wrapping angle of each layer remains the same along the entire length of the layer with the wrap angle of the individual layers changing to vary properly along the length of the catheter. However, if desired, the angle of wrap can be varied along the length of the tubular support member to vary the properties. The resin can be applied to the fiber material in any suitable manner.

In another presently preferred embodiment, the composite tubing of the invention is utilized as the tubular member in a low-profile steerable dilation catheter wherein a guidewire or guiding element is fixed within the dilation catheter. In this embodiment, an inflatable balloon element is provided on the distal end of the composite tubing with the inner lumen of the composite tubing adapted to direct inflating fluid in to the interior of the balloon. The fixed guiding element extends at least from the distal end of the balloon and has a helical coil or flexible tubular body disposed on the outer portion thereof. The distal end of the balloon is sealed about the guiding element or distal end of the tubular wire, whichever projects therethrough, to prevent the loss of inflating liquid.

In one preferred embodiment, the guide element is secured to the distal end of the tubular member and projects through the distal end of the balloon. In this case the proximal end of the composite tubing is provided with torquing means to guide the catheter. In another embodiment, the guide element extends through the inner lumen of the composite tubing from the proximal end thereof to the distal extremity of the catheter. In this embodiment, the guidewire is provided with a torquing knob at the proximal end thereof in a conventional manner to rotate the distal tip and thereby guide the catheter when it is being advanced through the patient's vascular system Further details of steerable dilatation catheters and the operation thereof can be found in U.S. Pat. No. 4,582,181 and U.S. patent application Ser. No. 000,650, filed Jan. 6, 1987, which are hereby incorporated herein in their entirety by reference thereto.

The dilatation catheters embodying features of the invention have substantially improved pushability and distal flexibility over prior catheters and the structure thereof ensures that the circularity of the transverse cross section of the composite tubular member is maintained even when the tubular catheter body is bent through arcs having relatively small radii of curvature. Moreover, the desired stiffness and flexibility can be varied over the length of the catheter. These and other advantages of the invention will become more apparent from the following detailed description of the invention when taken in conjunction with the accompanying exemplary drawings.

BRIEF DESCRIPTION OF THE DRAWINGS

FIG. 1 is a longitudinal view, partially in section, of a dilatation catheter embodying features of the invention;

FIG. 2 is a transverse cross-sectional view of the catheter shown in FIG. 1 taken along the lines 2—2;

FIG. 3 is a transverse cross-sectional view of the catheter shown in FIG. 1 taken along the lines 3—3;

DETAILED DESCRIPTION OF THE INVENTION

Figure 4:
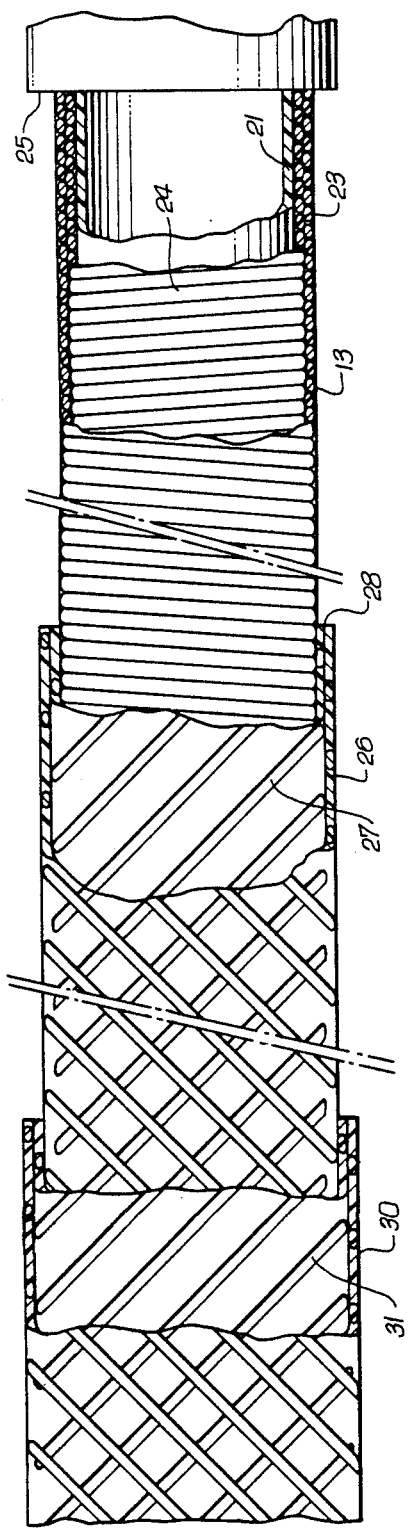
FIG. 4 is an enlarged view of the catheter section encircled by line 4—4.

FIGS. 1-3 illustrate a dilatation catheter assembly 10 embodying features of the invention which generally includes an outer tubular member 11 having an inflatable balloon member 12 on the distal portion thereof, an inner tubular member 13 of composite construction disposed within the outer tubular member 11 and defining an annular lumen 14 there between and an adapter 15 at the proximal end of the catheter 10 in fluid communication with the annular lumen 14 and adapted to supply inflation fluid thereto. Inner lumen 16 extends along the length of inner tubular member 13 and is adapted to slidably receive a guidewire 17.

The distal end 18 of the balloon member 12 may be sealed about the distal end 20 of inner tubular member 13 by applying an adhesive, heat shrinking the distal end 18, or other suitable means. Preferably, means (not shown) are provided at the distal end of catheter 10 to vent air from the interior of the balloon member 12 when it is inflated with inflation fluid. Suitable means to vent air which may be used are described in U.S. Pat. No. 4,638,805 (Powell) and co-pending applications Ser. No. 000,648 and 000,651, both filed Jan. 6, 1987. All are incorporated herein by reference thereto. Alternately, a conventional vent tube may be used.

The inner tubular member 13 has a composite structure in accordance with the present invention with a tubular, longitudinally inextensible substrate 21 and a resin-impregnated fibrous cover 22 surrounding and secured or bound thereto over a substantial portion of the length thereof. The details of the fibrous cover 22 are shown in the enlarged views of FIG. 4.

The innermost fibrous layer 23 of cover 22 comprises at least one fiber or strand 24 which is wrapped or braided about tubular substrate 21 at a wrap angle of about 60° to about 85° and impregnated with suitable resin. Wrapping of strand 24 begins at the distal end of tubular substrate 21 and continues to location 25 within the interior of balloon member 12 where the layer 23 terminates. The strand movement is then reversed to the proximal direction with the wrap angle essentially the same but in the opposite direction to provide flexibility to the uncovered portion thereof.

The second fibrous layer 26 comprises at least one fiber or strand 27 which is wrapped or braided about the previously applied layer 23 at an angle of orientation of about 30° to about 60° from the longitudinal axis of the tubular substrate 21 and impregnated with suitable resin. Second layer 26 terminates at location 28 proximally from the distal termination 25 of layer 23. The layer 26 provides increased stiffness and thus aids in the pushability thereof because of the wrap angle. A third layer 30 comprises one or more fibers or strands 31 wrapped at an angle of orientation similar to that of the second layer 26, but the layer 30 does not extend distally as far. The fibrous layers 26 and 30 are wrapped as the first layer 23 with a single strand in a direction of travel from the proximal end of tubular substrate 21, at the desired angle and then wrapped in a reversed proximal direction at essentially the same angle in the opposite direction of travel.

While each of the fibrous layers shown in FIG. 4 are wrapped at the same continuous angle along the length thereof, the wrap angle may be varied along the length of a layer. For example, the strand in one layer may be wrapped about the proximal portion of tubular substrate member 21 at an angle within the range of 30° to 60°, whereas in the distal portion, the wrap angle may be varied within the range of 60° to 85°. Preferably, each subsequently applied layer or group of layers, terminates proximal to the termination of the preceding layer to provide a gradual variation in stiffness of the composite structure towards the proximal end thereof and flexibility for distal direction.

Generally, decreasing the wrap angle of the individual with respect to the longitudinal axis of the substructure 21 increases the stiffness and thus pushability of the tubular member, whereas increasing the wrap angle of the individual strand increases the diametric rigidity of the tubular member without significantly reducing flexibility. Thus, by varying the wrap angle of the strands, the number of resin-impregnated fibrous layers, the length thereof, and the strength and lineal weight of the strands, catheters can be produced with wide variations of stiffness and pushability at the proximal end along with wide variation of desired diametric rigidity and longitudinal flexibility at the distal end. While only wrapping of the strands to form the composite is described herein, braiding or weaving or combinations of braiding or weaving and wrapping of strands about the tubular substructure can be employed.

In the presently preferred embodiment, the strands are high strength multi-filament plastic fiber such as aramid (Kevlar), nylon or polyester (Dacron). The fiber can be from about 30 to 225 denier, but typically 55 denier is employed in the first layer 23 adjacent the tubular substrate 21 and 195 denier is employed in subsequent layers. Suitable epoxy resins for impregnating the fibrous material are Hysol (No. 3561 Hardner and No. 2038 Resin) sold by Dexter Chemical Co. and Helozy (WC-8006) sold by Wilmington Chemical Corp.

The tubular substrate 21 is preferably of thin-walled construction it is longitudinally relatively flexible yet inextensible and it is diametrically relatively rigid. It may be formed from suitable plastic material such as polyimide or polyethylene. Polyimide is preferred because it can be made with a much thinner wall than polyethylene, thereby allowing greater reductions in overall catheter profile as is described in more detail in co-pending application Ser. No. 220,563, filed July 18, 1988, and entitled VASCULAR CATHETERS. The polyimide tubing having a wall thickness of less than about 0.003 inch (0.076 mm) and preferably within the range of about 0.00075 to about 0.0015 inch (0.0191 mm to 0.0381 mm), provides mechanical and physical properties comparable to conventionally used polyethylene and polyvinylchloride tubular products which have wall thicknesses many times thicker (e.g., 0.005 inch). One presently preferred thin-walled polyimide tubing is the MicroBore TM tubing manufactured by PolyMicro Technologies in Phoenix, Arizona. Another desirable polyimide tubing is manufactured from Matrimid TM 5218 from Ciba-Geigy Corp. of Hawthorn, New York. The polyimide tubing preferably may have an inner lubricious lining of polytetrafluoroethylene which may be formed simultaneously therewith or formed as a separate lining within the tubing. Further information regarding polyimide material may be found in A. Landis, "Commercial Polyimides," *Handbook of Thermoset Plastics*, Chapter 8, Edited by Sidney H. Goodman (1986), and E. Sacher, "A Reexamination of Polyimide Formation," *J. of Macromolecular Science-Physics*, Vol. B25, No. 4 (1986) pp 405–418, which are hereby incorporated by reference.

The other tubular members 11 of the catheter assembly 10 can be formed of conventional materials. For example, the outer tubular member 11 and balloon member 12 can be formed of irradiated polyethylene in a unitary structure or be constructed with the tubular portion 11 formed of polyethylene and the balloon member 12 formed of polyethylene terephthalate and secured to the distal end of the tubular member by suitable adhesive.

Typical diametrical dimensions of dilatation catheters in accordance with the present invention suitable for use with guide members of the indicated diameters are provided in the table below:

|  | Guide Member OD (inch) | | |
|---|---|---|---|
|  | 0.010 | 0.014 | 0.018 |
| ID Tubular Substrate | 0.013 | 0.017 | 0.0022 |
| OD Tubular Substrate | 0.015 | 0.019 | 0.0024 |
| OD Inner Tubular Member (A)* | 0.0185 | 0.0225 | 0.0275 |
| OD Inner Tubular Member (B)* | 0.0225 | 0.0265 | 0.0315 |
| OD Inner Tubular Member (C)* | 0.0265 | 0.0305 | 0.0355 |
| ID Outer Tubular Member | 0.0381 | 0.0381 | 0.042 |
| ID Outer Tubular Member | 0.047 | 0.047 | 0.051 |

*Letter locations on FIG. 1

Generally, the length of the catheter ranges from about 145 cm to about 175 cm.

Figure 5:
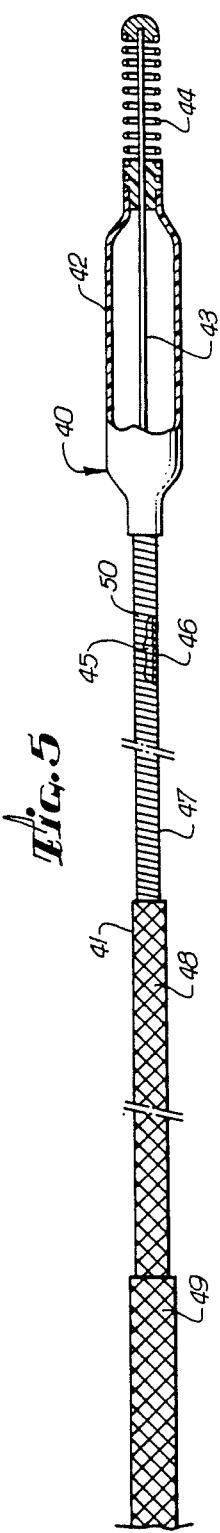
FIG. 5 is an elevation view partially in section of a steerable dilatation catheter embodying features of the invention.

FIG. 5 illustrates another presently preferred embodiment of the invention directed to a low-profile steerable catheter assembly 40 comprising a tubular member 41 of composite structure in accordance with the invention, a balloon member 42 secured to the distal end of composite tubular member 41, a fixed guide member 43 which extends out of the distal end of the balloon member 42 and helical coil 44 which is secured about the portion of the guide member 43 extending out of the distal end of balloon member 42. The tubular element 41 has an inner lumen 45 therein which is in fluid communication with the interior of balloon member 42 and is adapted to supply inflation fluid thereto.

The composite tubular member 41 of the embodiment shown in FIG. 5 is essentially of the same composite structure as shown in FIG. 1 for inner tubular member 13. Generally this structure comprises a tubular substrate 46, and fiber layers 47, 48, and 49. In the first layer 47, strand 50 is wrapped or braided at an angle with respect to the longitudinal axis of the tubular substructure of about 60° to about 85°. The wrap angle of the strands in the layers 47 and 48 are about 30° to about 60°.

The invention has been described herein primarily with reference to presently preferred embodiments. However, it should be recognized that various modifications and improvements can be made to the invention without departing from the scope thereof.

What is claimed is:

1. In a vascular dilation catheter for angioplasty procedures having an elongated outer tubular member which has a distal end, an inflatable balloon which has a distal end and which is on the distal end of the outer tubular member and an inner tubular member which has a distal end and an inner lumen adapted to receive a guidewire therein disposed within the outer tubular member forming therebetween an annular inflation lumen, the distal end of the inner tubular member being secured to the distal end of the balloon, the improvement in the catheter body comprising the inner tubular member having a tubular substructure and at least one fibrous, resin impregnated layer formed on the exterior thereof which provides longitudinal flexibility and diametric rigidity.

2. The vascular catheter of claim 1 wherein the fibrous layer on the exterior at the inner tubular member has a plurality of strand wraps in the distal portion thereof oriented at an angle with respect to the longitudinal axis of the tubular substrate of about 20° to about 45° greater than strand wraps in the proximal portion.

3. The vascular catheter of claim 2 wherein one or more strands in the distal portion are at an angle between about 60° and 85° with respect to the longitudinal axis of the tubular substrate.

4. The vascular catheter of claim 2 wherein a plurality of strand wraps in at least one of the layers in the proximal portion are oriented at an angle with respect to the longitudinal axis of the tubular substructure between about 30° and about 60°.

5. The vascular catheter of claim 2 wherein the strands are formed of multi-filament fibers made from a material selected from the group consisting of aramid, nylon and polyester, and are snugly wound about the tubular substructure and impregnated with resin.

6. The vascular catheter of claim 5 wherein strands in the proximal portion are longitudinally spaced from each other a distance of about 2-6 times the width of the wrapped strand and strands in the distal portion are wrapped adjacent to one another.

7. The vascular catheter of claim 5 wherein the impregnated resin is an epoxy resin.

8. The vascular catheter of claim 2 wherein each layer comprises at least one strand wound about the tubular substructure from the proximal end thereof to the distal termination of the layer and back to the proximal end.

9. The vascular catheter of claim 1 wherein the continuous strand is snugly wrapped along the substructure in one direction inclined toward the distal end of the tubular member and along the substructure in another direction inclined toward the proximal end of the tubular member.

10. A vascular dilation catheter assembly for performing angioplasty procedures comprising
   (a) an elongated outer tubular member with proximal and distal ends;
   (b) an inflatable balloon which has a distal end and which is on the distal end of the outer tubular member; and
   (c) an elongated inner tubular member which is disposed within the outer tubular member thereby forming an annular inflation lumen therebetween and which has a distal end bonded to the distal end of the balloon, the inner tubular member having an inner lumen adapted to receive a guidewire therein and, a tubular substructure and at least one fibrous, resin impregnated layer on the exterior thereof.

11. The dilation catheter of claim 10 wherein the fibrous layer has a plurality of strand wraps in the distal portion thereof oriented at an angle with respect to the longitudinal axis of the tubular substrate of about 20° to about 45° greater than strand wraps in the proximal portion.

12. The dilation catheter of claim 11 wherein a plurality of strand wraps in the distal portion are oriented at an angle between about 60° and about 85° with respect to the longitudinal axis of the tubular substrate.

13. The dilation catheter of claim 11 wherein a plurality of strand wraps in the proximal portion are oriented at an angle of from about 30° to about 60° with respect to the longitudinal axis of the tubular substrate.

14. The dilation catheter of claim 11 wherein the fibrous layer is formed by a continuous strand which is wound snugly about the tubular substrate and impregnated with resin.

15. The dilation catheter of claim 14 wherein the strands are formed from multi-filament fibers made from a material selected from the group consisting of aramid, nylon and polyester.

16. The dilatation catheter of claim 14 wherein the impregnated resin is an epoxy resin.

17. The dilation catheter of claim 14 wherein the strand wraps on the proximal portion are longitudinally spaced from each other a distance of about 2-6 times the width of the wrapped strand and the strand wraps in the distal portion are adjacent to one another.

18. The dilation catheter of claim 11 wherein each layer comprises at least one strand wound about the tubular substructure from the proximal end thereof to the distal termination of the layer and back to the proximal end.

19. The dilation catheter of claim 10 wherein the fibrous layer is formed by a continuous strand which is snugly wrapped along the substructure in one direction inclined toward the distal end of the tubular member and along the substructure in another direction inclined toward the proximal end of the tubular member.

20. The dilation catheter of claim 19 wherein the outer tubular member and the inflatable balloon are of unitary construction.

21. The dilation catheter of claim 19 wherein the balloon has a proximal end which is secured to the distal end of the outer tubular member.

22. The dilation catheter of claim 10 including an elongated guidewire slidably disposed within the inner lumen of the inner tubular member.

23. The dilation catheter of claim 10 wherein the outer tubular member and the inflatable balloon are of unitary construction.

24. The dilation catheter of claim 10 wherein the balloon has a proximal end which is secured to the distal end of the outer tubular member.

* * * * *